US008264362B2

(12) United States Patent
Ales, III et al.

(10) Patent No.: US 8,264,362 B2
(45) Date of Patent: Sep. 11, 2012

(54) EMBEDDED ANTENNA FOR SENSING ARTICLE

(75) Inventors: Thomas Michael Ales, III, Neenah, WI (US); Andrew Mark Long, Appleton, WI (US); Timothy Joseph Wurth, Fairfield, OH (US); Terrance James Hill, West Chester, OH (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 368 days.

(21) Appl. No.: 11/799,308

(22) Filed: Apr. 30, 2007

(65) Prior Publication Data

US 2008/0266123 A1    Oct. 30, 2008

(51) Int. Cl.
G08B 21/00    (2006.01)
G08B 13/14    (2006.01)
G08B 23/00    (2006.01)

(52) U.S. Cl. ..... 340/604; 340/603; 340/605; 340/572.1; 340/539.11; 340/539.15; 340/693.5; 340/573.1

(58) Field of Classification Search .......... None
See application file for complete search history.

(56) References Cited

U.S. PATENT DOCUMENTS

| | | | |
|---|---|---|---|
| 4,356,818 A | 11/1982 | Macias et al. | |
| 4,704,116 A | 11/1987 | Enloe | |
| 4,798,603 A | 1/1989 | Meyer et al. | |
| 4,940,464 A | 7/1990 | Van Gompel et al. | |
| 5,176,672 A | 1/1993 | Bruemmer et al. | |
| 5,486,166 A | 1/1996 | Bishop et al. | |
| 5,490,846 A | 2/1996 | Ellis et al. | |
| 5,509,915 A | 4/1996 | Hanson et al. | |
| 5,570,082 A | 10/1996 | Mahgerefteh et al. | |
| 5,704,352 A * | 1/1998 | Tremblay et al. | ............. 600/300 |
| 5,766,389 A | 6/1998 | Brandon et al. | |
| 5,820,973 A | 10/1998 | Dodge, II et al. | |
| 5,993,433 A | 11/1999 | St. Louis et al. | |
| 6,097,297 A | 8/2000 | Fard | |
| 6,248,097 B1 | 6/2001 | Beitz et al. | |
| 6,417,455 B1 | 7/2002 | Zein et al. | |
| 6,583,722 B2 | 6/2003 | Jeutter et al. | |
| 6,603,403 B2 | 8/2003 | Jeutter et al. | |
| 6,645,190 B1 | 11/2003 | Olson et al. | |
| 6,658,432 B1 | 12/2003 | Alavi et al. | |
| 6,753,783 B2 * | 6/2004 | Friedman et al. | .......... 340/573.7 |
| 6,916,968 B2 | 7/2005 | Shapira et al. | |
| 7,049,969 B2 * | 5/2006 | Tamai | ........................ 340/573.5 |
| 7,141,715 B2 | 11/2006 | Shapira | |
| 7,203,533 B1 * | 4/2007 | Tischer | ....................... 455/575.8 |

(Continued)

FOREIGN PATENT DOCUMENTS

DE    199 37 779 A1    2/2001

(Continued)

Primary Examiner — Julie Lieu
(74) Attorney, Agent, or Firm — Randall W. Fieldhack (57) ABSTRACT

Disclosed is an insult-sensing absorbent article including an absorbent assembly, an insult-sensing means coupled to the absorbent assembly, and a tuned antenna system coupled to the insult-sensing means. Also disclosed is a method for indicating an insult to an absorbent article to be worn by a wearer, the method including providing an absorbent article including a conductive element; providing an antenna system associated with the absorbent article, the antenna system including a signal generator and an antenna, wherein the antenna includes the conductive element, and wherein the antenna system is adapted to transmit a signal; and maximizing the receivability of the signal by optimizing an aspect of the antenna system.

13 Claims, 6 Drawing Sheets

U.S. PATENT DOCUMENTS

| | | | |
|---|---|---|---|
| 2002/0070864 A1* | 6/2002 | Jeutter et al. | 340/573.1 |
| 2002/0070868 A1* | 6/2002 | Jeutter et al. | 340/604 |
| 2004/0036484 A1* | 2/2004 | Tamai | 324/663 |
| 2004/0064114 A1 | 4/2004 | David et al. | |
| 2005/0156744 A1* | 7/2005 | Pires | 340/573.5 |
| 2006/0220869 A1* | 10/2006 | Kodukula et al. | 340/572.7 |
| 2007/0049881 A1 | 3/2007 | Ales et al. | |
| 2007/0252710 A1 | 11/2007 | Long et al. | |
| 2007/0252711 A1 | 11/2007 | Long et al. | |
| 2007/0252712 A1 | 11/2007 | Allen et al. | |
| 2008/0004904 A1* | 1/2008 | Tran | 705/2 |
| 2008/0024301 A1* | 1/2008 | Fritchie et al. | 340/572.1 |

FOREIGN PATENT DOCUMENTS

| | | |
|---|---|---|
| EP | 1 057 150 B1 | 10/2002 |
| JP | 64-025049 A | 1/1989 |
| JP | 2001-134726 A | 5/2001 |
| JP | 2005-000602 A | 1/2005 |
| WO | WO 99/62041 A1 | 12/1999 |
| WO | WO 00/37009 A2 | 6/2000 |
| WO | WO 03/027636 A2 | 4/2003 |
| WO | WO 2004/038342 A2 | 5/2004 |
| WO | WO 2005/067836 A1 | 7/2005 |
| WO | WO 2007/038990 A1 | 4/2007 |

* cited by examiner

EMBEDDED ANTENNA FOR SENSING ARTICLE

BACKGROUND

Absorbent articles such as diapers, training pants, incontinence products, feminine hygiene products, swim undergarments, and the like, conventionally include a liquid permeable body-side liner, a liquid impermeable outercover, and an absorbent core. The absorbent core is typically located between the outercover and the liner for taking in and retaining liquids (e.g., urine) exuded by the wearer.

Many absorbent articles have been adapted for use in a training program, such as toilet training or enuresis control, or to provide indication of various medical, physical, or other conditions. Accordingly, various types of sensors and indicators, including moisture or wetness indicators, have been suggested for use in absorbent articles. Wetness indicators, for example, may include alarm devices that are designed to assist parents or attendants to identify a wet diaper condition quickly upon insult. The devices produce either a visual or an audible signal.

In some aspects, for instance, inexpensive conductive threads or foils have been placed in the absorbent articles. The conductive materials serve as conductive leads for a signaling device and form an open circuit in the article that can be closed when a body fluid, such as urine, closes the circuit. In other aspects, various other sensors have been included in absorbent articles, where the sensors may communicate test results, indications, or other data to a wearer or a caregiver via a signaling device. Attempts have been made to use conductive elements as an antenna, but these have been without regard to efficiency, optimization, or accounting for the effects of the wearer's body, clothing, or movement and therefore have not been implemented.

SUMMARY

In these aspects of the present disclosure, the signaling devices may wirelessly transmit a signal to a caregiver or a monitor because it is beneficial to the caregiver and wearer that the technology be as non-invasive as possible (e.g., reduced cables and hardware). To achieve this, wireless transmitters, receivers, and transceivers, as they are smaller, more powerful, and flexible, are beginning to play a crucial role.

Wireless monitoring of a human subject, however, is an extremely complex technical challenge. When placing a wireless transmitter in close proximity with the human body, the antenna is not allowed to transmit data under optimal conditions; human tissue works as an electromagnetic absorber so the power of the transmitted signal that is seen by the receiver is dependent on the interaction of the antenna with the body, the proximity of the receiver, and the orientation of the antenna. To complicate this, a transmitter placed on a wearer may be located in a position between the body and another radio frequency-obstructive material such as clothing, furniture, the ground, architecture, etc. These conditions not only affect the signal integrity of the transmitter, but also greatly reduce the range of data transmission. These difficulties can require a stronger wireless signal and increased power consumption to overcome the potential signal-degrading effects of the body, clothing, and other interferences, thus translating to a loss in benefit to the consumer.

If wireless monitoring is to be successful, it should transmit accurate data throughout familiar environments such as a home or shopping mall and not be plagued by interference from bodily and environmental radio frequency obstructions.

The disclosure herein solves the problems described above and provides an increase in efficacy in using wetness and other sensors in absorbent articles by increasing the effectiveness with which wireless sensing components can be used. In general, the present disclosure is directed to sensing absorbent articles with easy-to-use wireless signaling devices. The signaling device, for instance, may be configured to indicate to a wearer that a body fluid is present in the sensing absorbent article.

For example, in one aspect of the present disclosure, the disclosure includes an insult-sensing absorbent article including an absorbent assembly, an insult-sensing means coupled to the absorbent assembly, and a tuned antenna system coupled to the insult-sensing means.

In another aspect of the present disclosure, the disclosure includes a method for indicating an insult to an absorbent article to be worn by a wearer, the method including providing an absorbent article including a conductive element; providing an antenna system associated with the absorbent article, the antenna system including a signal generator and an antenna, wherein the antenna includes the conductive element, and wherein the antenna system is adapted to transmit a signal; and maximizing the receivability of the signal by optimizing an aspect of the antenna system.

BRIEF DESCRIPTION OF THE DRAWINGS

The foregoing and other features and aspects of the present disclosure and the manner of attaining them will become more apparent, and the disclosure itself will be better understood by reference to the following description, appended claims and accompanying drawings, where:

Repeat use of reference characters in the present specification and drawings is intended to represent the same or analogous features or elements of the present disclosure. The drawings are representational and are not necessarily drawn to scale. Certain proportions thereof may be exaggerated, while others may be minimized.

DETAILED DESCRIPTION

It is to be understood by one of ordinary skill in the art that the present discussion is a description of exemplary aspects of the present disclosure only, and is not intended as limiting the broader aspects of the present disclosure.

The present disclosure is generally directed to sensing absorbent articles adapted to be attached to a signaling device that may be configured to indicate the presence of a body fluid in the absorbent article or other changes in the condition of the product or wearer. The absorbent article may be, for instance, a diaper, a training pant, a pre-fastened pant, a swimming pant, an incontinence product, a feminine hygiene product, a medical garment, a bandage, or any other suitable article.

The disclosure described herein may be used with any type of sensing article. In one type of training pant sensing article used as a non-limiting example herein, insult-sensing absorbent articles may include an open circuit that becomes closed when a conductive fluid, such as a body fluid, is present between a pair of conductive leads. Alternatively, insult-sensing absorbent articles may include a closed circuit that becomes open when a fluid, such as a body fluid, is present. Generally, the insult-sensing absorbent articles containing the circuit are disposable, meaning that they are designed to be discarded after a limited use rather than being laundered or otherwise restored for reuse.

The circuit contained within the insult-sensing absorbent articles of the present disclosure is configured to be attached to a signaling device. The signaling device can provide power to the circuit while also including some type of audible, visible and/or electromagnetic signal that indicates to the wearer the presence of a body fluid. Although the insult-sensing absorbent article may itself be disposable, the signaling device may be reusable from article to article. In this regard, the present disclosure is particularly directed to different types of attachment mechanisms that allow easy connection between the circuit in the insult-sensing absorbent article and the signaling device.

As described above, the circuit in combination with the signaling device may be configured to indicate the presence of a body fluid contained within the insult-sensing absorbent article. The particular targeted body fluid may vary depending upon the particular type of insult-sensing absorbent article and the desired application. For instance, in one aspect of the present disclosure, the insult-sensing absorbent article comprises a diaper, a training pant, or the like and the signaling device is configured to indicate the presence of urine. Alternatively, the signaling device may be configured to indicate the presence of a metabolite that would indicate the presence of a diaper rash. For adult incontinence products and feminine hygiene products, on the other hand, the signaling device may be configured to indicate the presence of a yeast or of a particular constituent in urine or menses, such as a polysaccharide.

Figure 1:
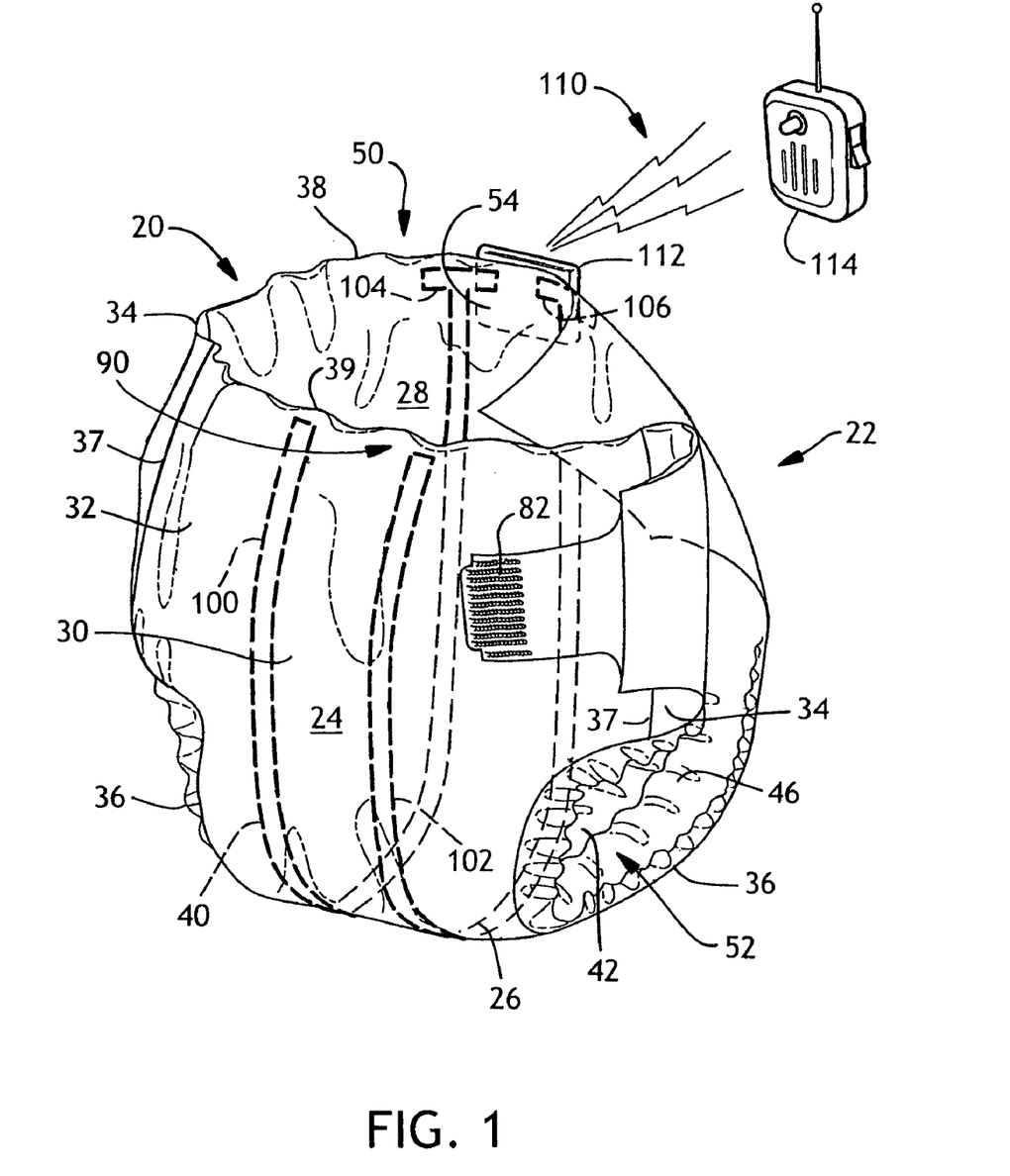
FIG. 1 is a perspective view of an absorbent article of the present disclosure.

Referring to FIG. 1, for non-limiting exemplary purposes, a insult-sensing absorbent article 20 is shown. The insult-sensing absorbent article 20 may or may not be disposable. It is understood that the present disclosure is suitable for use with various other insult-sensing absorbent articles intended for personal wear, including but not limited to diapers, training pants, swim pants, feminine hygiene products, incontinence products, medical garments, surgical pads and bandages, other personal care or health care garments, and the like, without departing from the scope of the present disclosure.

By way of illustration only, various materials and methods for constructing insult-sensing absorbent articles such as the insult-sensing absorbent article 20 of the various aspects of the present disclosure are disclosed in U.S. Pat. No. 4,798,603 issued Jan. 17, 1989, to Meyer et al.; U.S. Pat. No. 5,176,672 issued Jan. 5, 1993, to Bruemmer et al., U.S. Pat. No. 5,509, 915 issued Apr. 23, 1996 to Hanson et al., U.S. Pat. No. 5,993,433 issued Nov. 30, 1999 to St. Louis et al.; U.S. Pat. No. 6,248,097 issued Jun. 19, 2001 to Beitz et al.; PCT Patent Application WO 00/37009 published Jun. 29, 2000 by A. Fletcher et al.; U.S. Pat. No. 4,940,464 issued Jul. 10, 1990 to Van Gompel et al.; U.S. Pat. No. 5,766,389 issued Jun. 16, 1998 to Brandon et al.; and U.S. Pat. No. 6,645,190 issued Nov. 11, 2003 to Olson et al. which are incorporated herein by reference to the extent they are consistent (i.e., not in conflict) herewith.

A insult-sensing absorbent article 20 is representatively illustrated in FIG. 1 in a partially fastened condition.

The insult-sensing absorbent article 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The insult-sensing absorbent article 20 also defines an inner surface 28 adapted in use (e.g., positioned relative to the other components of the article 20) to be disposed toward the wearer, and an outer surface 30 opposite the inner surface. The front and back regions 22, 24 are those portions of the insult-sensing absorbent article 20, which when worn, wholly or partially cover or encircle the waist or mid-lower torso of the wearer. The crotch region 26 generally is that portion of the insult-sensing absorbent article 20 which, when worn, is positioned between the legs of the wearer and covers the lower torso and crotch of the wearer. The insult-sensing absorbent article 20 has a pair of laterally opposite side edges 36 and a pair of longitudinally opposite waist edges, respectively designated front waist edge 38 and back waist edge 39.

The illustrated insult-sensing absorbent article 20 includes a chassis 32 that, in this aspect of the present disclosure, encompasses the front region 22, the back region 24, and the crotch region 26. The chassis 32 includes an outercover 40 and a bodyside liner 42 that may be joined to the outercover 40 in a superimposed relation therewith by adhesives, ultrasonic bonds, thermal bonds or other conventional techniques. The liner 42 can be generally adapted, i.e., positioned relative to the other components of the article 20, to be disposed toward the wearer's skin during wear of the insult-sensing absorbent article. The chassis 32 may further include an absorbent structure 44 (see FIGS. 2-4) disposed between the outercover 40 and the bodyside liner 42 for absorbing liquid body exudates exuded by the wearer, and may further include a pair of containment flaps 46 secured to the bodyside liner 42 for inhibiting the lateral flow of body exudates. Suitable constructions and arrangements for the containment flaps 46 are generally well known to those skilled in the art and are described in U.S. Pat. No. 4,704,116 issued Nov. 3, 1987 to Enloe, which is incorporated herein by reference to the extent they are consistent (i.e. not in conflict) herewith.

To further enhance containment and/or absorption of body exudates, the insult-sensing absorbent article 20 may also suitably include leg elastic members (not shown), as are known to those skilled in the art.

In some aspects of the present disclosure, the insult-sensing absorbent article 20 may further include a surge management layer (not shown) that may be optionally located adjacent the absorbent structure 44 and attached to various components in the article 20 such as the absorbent structure 44 or the bodyside liner 42 by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. No. 5,486,166 and U.S. Pat. No. 5,490,846. Other suitable surge management materials are described in U.S. Pat. No. 5,820,973. The entire disclosures of these patents are hereby incorporated by reference herein to the extent they are consistent (i.e., not in conflict) herewith.

As shown in FIG. 1, the insult-sensing absorbent article 20 further includes a pair of opposing elastic side panels 34 that are attached to the back region of the chassis 32. As shown particularly in FIG. 1, the side panels 34 may be stretched around the waist and/or hips of a wearer to secure the garment in place. The elastic side panels are attached to the chassis 32 along a pair of opposing longitudinal edges 37. The side panels 34 may be attached or bonded to the chassis 32 using any suitable bonding technique. For instance, the side panels 34 may be joined to the chassis 32 by adhesives, ultrasonic bonds, thermal bonds, or other conventional techniques. Ultimately, the side panels 34 are generally aligned with a waist region 90 of the chassis 32.

In an alternative aspect of the present disclosure, the elastic side panels may also be integrally formed with the chassis 32. For instance, the side panels 34 may comprise an extension of the bodyside liner 42, of the outercover 40, or of both the bodyside liner 42 and the outercover 40.

The side panels 34 are connected to the back region of the insult-sensing absorbent article 20 and extend over the front region of the article when securing the article in place on a wearer. It should be understood, however, that the side panels 34 may alternatively be connected to the front region of the article 20 and extend over the back region when the article is donned.

With the insult-sensing absorbent article 20 in the fastened position as partially illustrated in FIG. 1, the elastic side panels 34 may be connected by a fastening system 82 to define a 3-dimensional insult-sensing absorbent article configuration having a waist opening 50 and a pair of leg openings 52. The waist opening 50 of the article 20 is defined by the waist edges 38 and 39 which encircle the waist of the wearer.

In the aspects of the present disclosure shown in the figures, the side panels are releasably attachable to the front region 22 of the article 20 by the fastening system 82. It should be understood, however, that in other aspects of the present disclosure the side panels may be permanently joined to the chassis 32 at each end. The side panels may be permanently bonded together, for instance, when forming a training pant or absorbent swimwear.

The fastening system 82 may include laterally opposite first fastening components adapted for refastenable engagement to corresponding second fastening components. The fastening system 82 may include any refastenable fasteners suitable for insult-sensing absorbent articles, such as adhesive fasteners, cohesive fasteners, mechanical fasteners, or the like. In particular aspects, the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In addition to possibly having elastic side panels, the insult-sensing absorbent article 20 may include various waist elastic members for providing elasticity around the waist opening. For example, as shown in the figures, the insult-sensing absorbent article 20 can include a front waist elastic member 54 and/or a back waist elastic member (not shown).

As described above, the present disclosure is particularly directed to incorporating a body fluid indicating system. One such system is described below. Other systems include a wetness liner such as that described in U.S. Pat. No. 6,658,432 to Underhill et al., a temperature system, a system in which graphics fade or appear, and any other suitable body fluid indicating system.

One such body fluid indicating system is the insult-sensing indicating system described herein. In this regard, as shown in FIG. 1, the insult-sensing absorbent article 20 includes a first conductive element 100 spaced from a second conductive element 102. In this aspect of the present disclosure, the conductive elements extend from the front region 22 of the insult-sensing absorbent article to the back region 24 without intersecting. The conductive elements 100 and 102 can include any suitable conductive material, such as a conductive thread or a conductive foil including, for example, 112-S silver metallic conductive paste (ink) from Electroscience Laboratories, Inc. and conductive foil described in U.S. Pat. No. 6,417,455 issued Jul. 9, 2002 to Zein et al. The first conductive element 100 may not intersect the second conductive element 102 in order to form an open circuit that may be closed, for instance, when a conductive fluid is positioned in between the conductive elements. In other aspects of the present disclosure, however, the first conductive element 100 and the second conductive element 102 may be connected to a sensor within the chassis 32. The sensor may be used to sense changes in temperature or may be used to sense the presence of a particular substance, such as a metabolite.

In the aspect of the present disclosure shown in FIG. 1, the conductive elements 100 and 102 extend the entire length of the insult-sensing absorbent article 20. It should be understood, however, that in other aspects of the present disclosure, the conductive elements may extend only to the crotch region 26 or may extend to any particular place in the insult-sensing absorbent article where a body fluid is intended to be sensed.

The conductive elements 100 and 102 may be incorporated into the chassis 32 at any suitable location as long as the conductive elements are positioned so as to contact a body fluid that is absorbed by the insult-sensing absorbent article 20. In this regard, the conductive elements 100 and 102 generally lie inside the outercover 40. In fact, in one aspect of the present disclosure, the conductive elements 100 and 102 may be attached or laminated to the inside surface of the outercover 40 that faces the absorbent structure. Alternatively, however, the conductive elements 100 and 102 may be positioned on the absorbent structure or positioned on the liner 42.

The conductive elements 100 and 102 may be connected directly to a signaling device, either through direct or indirect contact. The first conductive element 100 may be attached to a first conductive pad member 104, while the second conductive element 102 may be connected to a second conductive pad member 106. The pad members 104 and 106 may be provided for making a reliable connection between the open circuit formed by the conductive elements to a signaling device that is intended to be installed on the chassis 32 by the consumer or manufacturer. The pad members 104 and 106 may create a zone for connecting the signaling device and the conductive leads or elements.

The conductive pad members 104 and 106 may have a relatively large surface area in relation to the conductive elements 100 and 102. For example, the conductive pad members 104 and 106 may have a surface area of at least 0.5 $cm^2$, at least 1 $cm^2$, at least 2 $cm^2$, and, in another aspect of the present disclosure, at least 3 $cm^2$. For instance, in another aspect of the present disclosure, the surface area of each pad member may be from about 2 $cm^2$ to about 4 $cm^2$.

The position of the conductive pad members 104 and 106 on the insult-sensing absorbent article 20 can vary depending upon where it is desired to mount the signaling device. For instance, in FIG. 1, the conductive pad members 104 and 106 are positioned in the front region 22 along the waist opening of the article. In another aspect of the present disclosure that is not shown, the conductive pad members 104 and 106 are positioned in the back region 24 along the waist opening of the article. It should be appreciated, however, that in other aspects of the present disclosure, the insult-sensing absorbent article 20 may include conductive pad members 104 and 106 being positioned at each end of each conductive element 100 and 102. In still other aspects of the present disclosure, it should be understood that the pad members 104 and 106 may be located along the side of the article or towards the crotch region of the article.

The position of the conductive pad members 104 and 106 within the multiple layers of the chassis 32 may also vary depending upon where it is desired to connect the signaling device and the type of attachment mechanism used to make a connection with the signaling device. As described above, the pad members 104 and 106 are electrically connected to the conductive elements 100 and 102. Thus, in one aspect of the present disclosure, the pad members 104 and 106 are positioned below (toward the body side) at least one layer of the outercover 40. Positioning the pad members 104 and 106 below at least one layer of material may provide various advantages in some aspects of the present disclosure. For instance, locating the pad members 104 and 106 below at least one layer of material within the chassis 32 protects the pad members during shipping and storage and from forming a short circuit during use especially if the pad members are located adjacent one another. Another benefit to placing the pad members under at least one layer of material is the ability to easily manufacture the insult-sensing absorbent article 20 at high machine speeds.

It should be understood, however, that in other aspects of the present disclosure the conductive pad members 104 and 106 may be positioned at an exterior surface of the chassis 32. For instance, the pad members 104 and 106 may be positioned on the outside surface or on the inside surface as desired.

Further details related to the structure, features, and materials of the absorbent article 20 may be found in co-pending and co-assigned U.S. patent application Ser. No. 11/414,032, filed on Apr. 27, 2006 by Allen, et al. and titled "An Array of Wetness Sensing Articles"; which is incorporated herein by reference to the extent it is consistent (i.e., not in conflict) herewith.

Referring to FIG. 1 for exemplary purposes, a signaling device 110 (as depicted by ref. numerals 112 and 114) is shown attached to the conductive pad members 104 and 106. As shown, in this aspect of the present disclosure, the signaling device 110 generally includes a transmitter 112 and a receiver 114. The transmitter 112 includes a pair of opposing terminals that are electrically connected to the corresponding conductive elements. When a body fluid is present in the insult-sensing absorbent article 20, the open circuit formed by the conductive elements 100 and 102 is closed which, in turn, activates the signaling device 110. In particular, in this aspect of the present disclosure, the transmitter 112 sends a wireless signal to the receiver 114 which then indicates to a wearer or caregiver that a body fluid is present in the insult-sensing absorbent article 20. In other various aspects of the present disclosure, any chemical or physical reaction that can change conductivity can also be sensed by this type of system—examples include conductivity changes associated with electrochemical sensors inside of the absorbent article 20 such as those described in co-pending and co-assigned U.S. patent application Ser. No. 11/314,438, filed on Dec. 21, 2005 by Ales, et al. and titled "Personal Care Products with Microchemical Sensors for Odor Detection"; which is incorporated herein by reference to the extent it is consistent (i.e., not in conflict) herewith.

The signaling device 110 can emit an audible signal or a visual signal to indicate to the wearer that the circuit has been closed. The audible signal, for instance, may be as simple as one or more beeps or may emit a musical tune. Similarly, if the signaling device 110 issues a visible signal, the visible signal may comprise one light, a few lights, or an interactive display. In still another aspect of the present disclosure, the receiver 114 of the signaling device 110 may be configured to vibrate when the circuit within the insult-sensing absorbent article is closed.

In the aspect of the present disclosure shown in FIG. 1, the signaling device 110 includes a transmitter 112 in combination with a receiver 114. It should also be understood, however, that the signaling device may comprise a single unit that remains attached to the insult-sensing absorbent article 20. For example, the signaling device may be mounted on the insult-sensing absorbent article and issue a visible signal and/or an audible signal from the article itself.

In various aspects of the present disclosure, the insult-sensing absorbent article 20 may include additional features such as those disclosed in co-pending and co-assigned U.S. patent application Ser. No. 11/303,283 to Long, et al. and entitled "Garments With Easy-To-Use Signaling Device"; and U.S. patent application Ser. No. 11/215,937 to Ales, et al. and entitled "Method of Detecting the Presence of an Insult in an Absorbent Article and Device for Detecting the Same"; which are incorporated herein by reference to the extent they are consistent (i.e., not in conflict) herewith. For example, the insult-sensing absorbent article may also include other insult-sensing features such as fading ink, appearing ink, a wetness liner, or a cooling component.

The insult-sensing absorbent article 20 may be a part of a insult-sensing system such as those described in above-referenced co-pending and co-assigned U.S. patent application Ser. No. 11/414,032, filed on Apr. 27, 2006 by Allen, et al. and titled "An Array of Wetness Sensing Articles.".

In addition to the aspects described above, the signaling device 110 may also be provided with a means for signaling the caregiver that the signaling device 110 is properly connected to the absorbent article 20, including a confirmatory visual or auditory signal when the signaling device 110 is properly connected. Further discussion on these aspects is provided in co-pending and co-assigned U.S. patent application Ser. Nos. 11/412,351, filed on Apr. 26, 2006 by Long et al. and titled "Wetness Monitoring Systems With Status Notification System"; and 11/412,364, filed on Apr. 26, 2006 by Long et al. and titled "Wetness Monitoring Systems With Power Management"; which are incorporated herein by reference to the extent they are consistent (i.e., not in conflict) herewith.

One way of enhancing the effectiveness and convenience of a sensing article is to provide a wireless interface employing an optimized antenna system. An optimized antenna system will minimize power consumption, thus maximizing the usefulness of the signaling device 110. An optimized antenna system will also allow the signaling device 110 to be used in situations in which long-range wireless transmissions are desired or to be avoided. An optimized antenna system also, allows the integrity of a transmitted signal to be maximized. The antenna system includes an antenna 120 (see FIGS. 2 and 3) and additional signal-handling components that can be included in the signaling device 110 or in any other suitable arrangement.

A number of variables can be adjusted to optimize the antenna system of the present disclosure.

First, the frequency of the signal is selected. Two primary considerations affect the selection of an appropriate frequency band: physics and regulations. Physics generally constrains the selection to a loosely defined range from several tens of megahertz (MHz) to perhaps several hundred MHz. Frequencies lower than about 100 MHz will cause the antenna efficiency to drop to the point that impractical amounts of power would be required. Frequencies above about 1 gigahertz (GHz) might make many household objects (including people) serious attenuators, again driving up the required transmission power.

Within this very broad range, regulatory issues can drive the design, because the sheer number of regulatory agencies becomes the first impediment. In the United States, the Federal Communications Commission regulates commercial uses of the frequency spectrum, while the National Telecommunications and Information Administration (NTIA) Manual of Regulations and Procedures for Federal Radio Frequency Management (Redbook) addresses government uses. Although the antenna system described herein does not fall under the purview of the NTIA, consideration must be given to potential interference sources allowed for government use. On a global scale, the International Telecommunications Union (ITU) is the steering body. Unfortunately, each government is free to disregard the ITU recommendations, and many do, because the ITU recommendations are only recommendations (see www.itu.int/publications/default.aspx). Further complicating matters is the fact that the World Radio Conference, hosted by the ITU every 3 or 4 years, can make changes in the recommendations.

To resolve these potentially adverse considerations, most countries have one or more bands for short range, intermittent transmissions such as garage door openers and remote keyless entry systems. Selecting a frequency within those bands, which will almost certainly be within the range allowed by physics, will allow approval for operation.

In other words, selecting a frequency considers unlicensed frequencies and the frequencies of other signals that may interfere with that of the signaling device 110. Criterion for selecting a frequency also include selecting an unlicensed, easy-to-use frequency, preferably in the radio frequency ranges below microwave frequencies, generally below 1 GHz, due to the potential for biological interaction. The frequency can also be above 100 MHz or so for easy-to-use and practical antenna lengths and powers. There are three commonly-used frequency bands set aside in the United States for devices in common use in a household setting. These are 315, 433, and 915 MHz. While any of these may be suitable, the 915 MHz frequency has many conflicting uses (e.g., key fobs, door openers, cordless telephones, computer networks, wireless speakers and headphones) in a household setting and is therefore a less desirable choice for use as a carrier frequency. For the reasons explained below, the 433 MHz frequency will be used in the examples presented herein.

Second, the length of the antenna 120 can be adjusted to maximize the integrity and range of the transmitted signal by adjusting the antenna length such that it corresponds to the wavelength of the signal. For example, the antenna 120 may be sized such that its length is at least one-quarter of the wavelength of the selected frequency. At 433 MHz, the quarter-wave antenna length is 173 mm. If antenna length were the only criterion, the 433 MHz frequency would be more desirable than the 315 MHz frequency because the quarter-wave antenna length for the latter is 238 mm. Because the quarter-wave antenna length for a 915 MHz signal is only 82 mm, that frequency might also be less desirable if the short antenna length accentuates the occlusive effects of a wearer's body, clothing, and movement.

Choosing a lower frequency means choosing a longer wavelength; this requires a longer antenna 120. While coiled and flat antennas are available, their ability to send a clear signal can be limited. This effect is magnified in the situations described herein because the antenna "footprint" on the body is small, so body position becomes a real limitation to reliable transmission.

Figure 2:
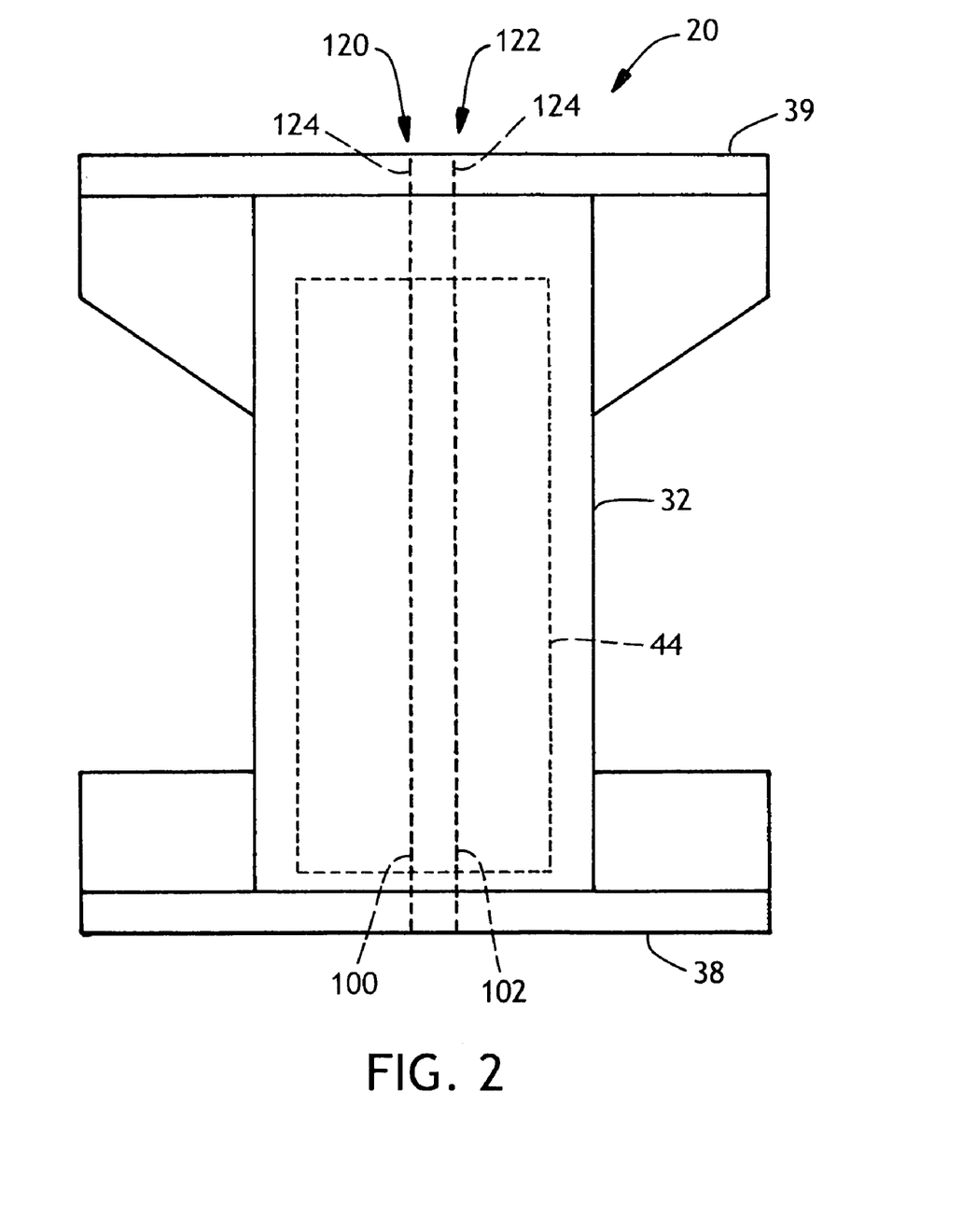
FIG. 2 is a schematic plan view of an aspect of the absorbent article of FIG. 1.

The form of the antenna 120 can be selected to minimize its size and maximize its effectiveness. The three most common antenna designs are folded dipole 124, monopole 122, and loop 126; all of these were tried as described below. The antenna 120 can be of any of these or other typical functional antenna designs. Derivations of these typical antenna designs, such as a meandered line antenna, or any other suitable antenna form can also be used. The insult-sensing absorbent article 20 disclosed herein includes conductive elements 100 and 102 that run the length or nearly the length of the product as illustrated in FIG. 2. In various aspects of the present disclosure, one or more of the conductive elements 100 and 102 can be used as the antenna 120. In other aspects of the present disclosure, an antenna 120 can be added to the insult-sensing absorbent article 20 in addition to the conductive elements 100 and 102.

For example, the monopole antenna aspect can be executed by using one of the conductive elements 100 and 102 as the monopole antenna 122, or by placing another conductive element into the insult-sensing absorbent article 20. If the monopole antenna 122 is separate from the conductive elements 100 and 102, the monopole antenna can be placed anywhere in the z-direction, where the z-direction is out of the plane of the insult-sensing absorbent article 20, or anywhere in x- or y-direction (the plane of the insult-sensing absorbent article 20), so as long as the monopole antenna 122 is not in contact with the conductive elements 100 and 102, or folded upon itself.

In another aspect of the present disclosure, the folded dipole antenna aspect can be executed by using both of the conductive elements 100 and 102 as the antenna 124, or by placing two new conductors in the insult-sensing absorbent article 20. If the folded dipole antenna 124 is separate from the conductive elements 100 and 102, the folded dipole antenna 124 can be placed anywhere in the z-direction, where the z-direction is out of the plane of the insult-sensing absorbent article 20, or anywhere in x- or y-direction (the plane of the insult-sensing absorbent article 20), so as long as the poles are not in contact with the conductive elements 100 and 102, folded upon themselves, or twisted with each other.

Figure 3:
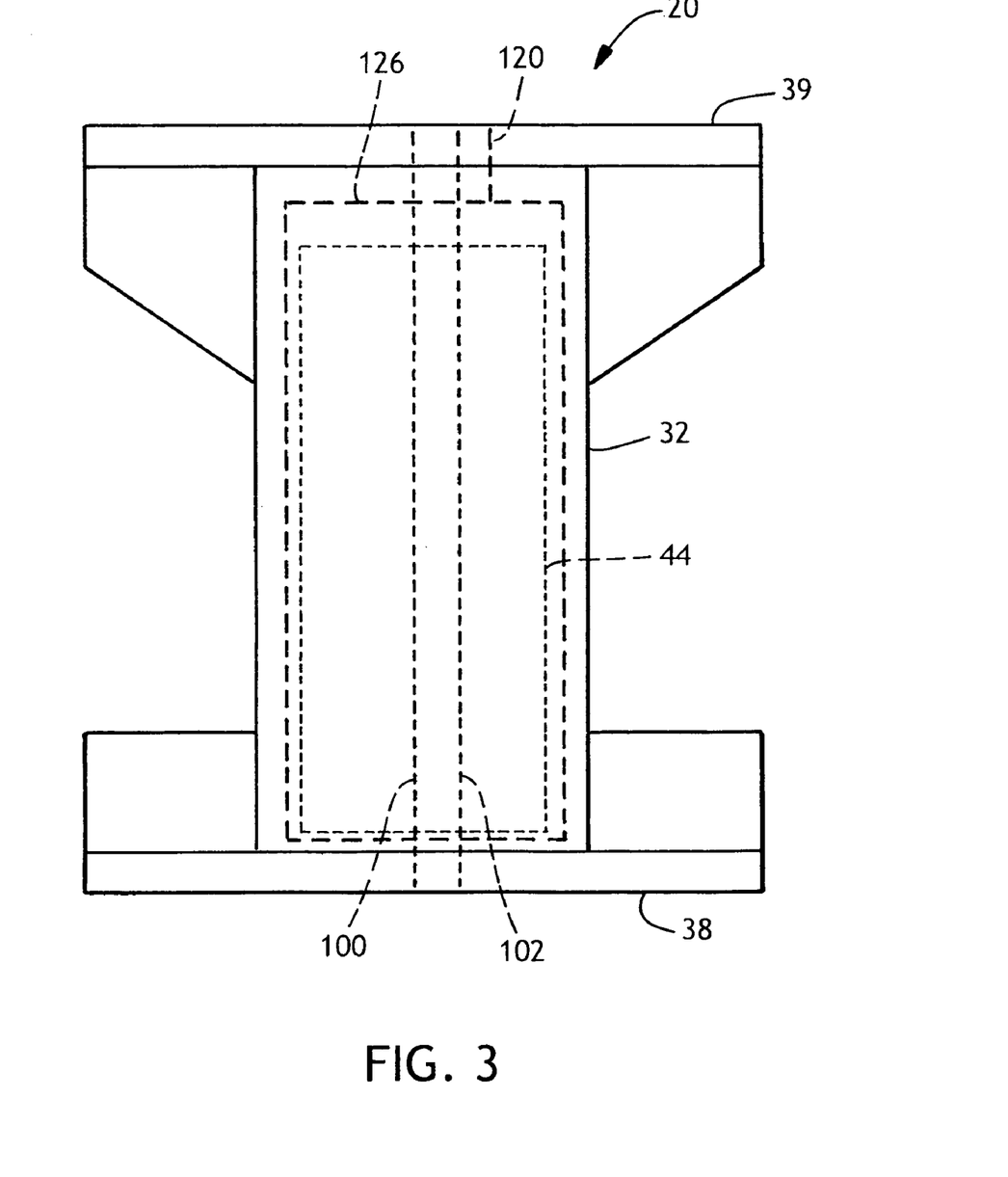
FIG. 3 is a schematic plan view of another aspect of the absorbent article of FIG. 1.

In another aspect of the present disclosure, the loop antenna embodiment can be executed by placing conductive material in the insult-sensing absorbent article 20 and by configuring the conductive material in any manner as long as it completes a circuit loop 126, as illustrated in FIG. 3. For example, the conductive material may be run along one side of the insult-sensing absorbent article 20, may be run in different patterns, etc. If the loop antenna 126 is separate from the conductive elements 100 and 102, the loop antenna 126 can be placed anywhere in the z-direction, where the z-direction is out of the plane of the insult-sensing absorbent article 20, or anywhere in x- or y-direction (the plane of the insult-sensing absorbent article 20), so as long as the loop antenna 126 completes a loop without contacting other parts of the loop. For example, the loop antenna 126 may be positioned on the outercover 40, between absorbent structure 44 and the bodyside liner 42, or adjacent the surge management layer.

Figure 4:
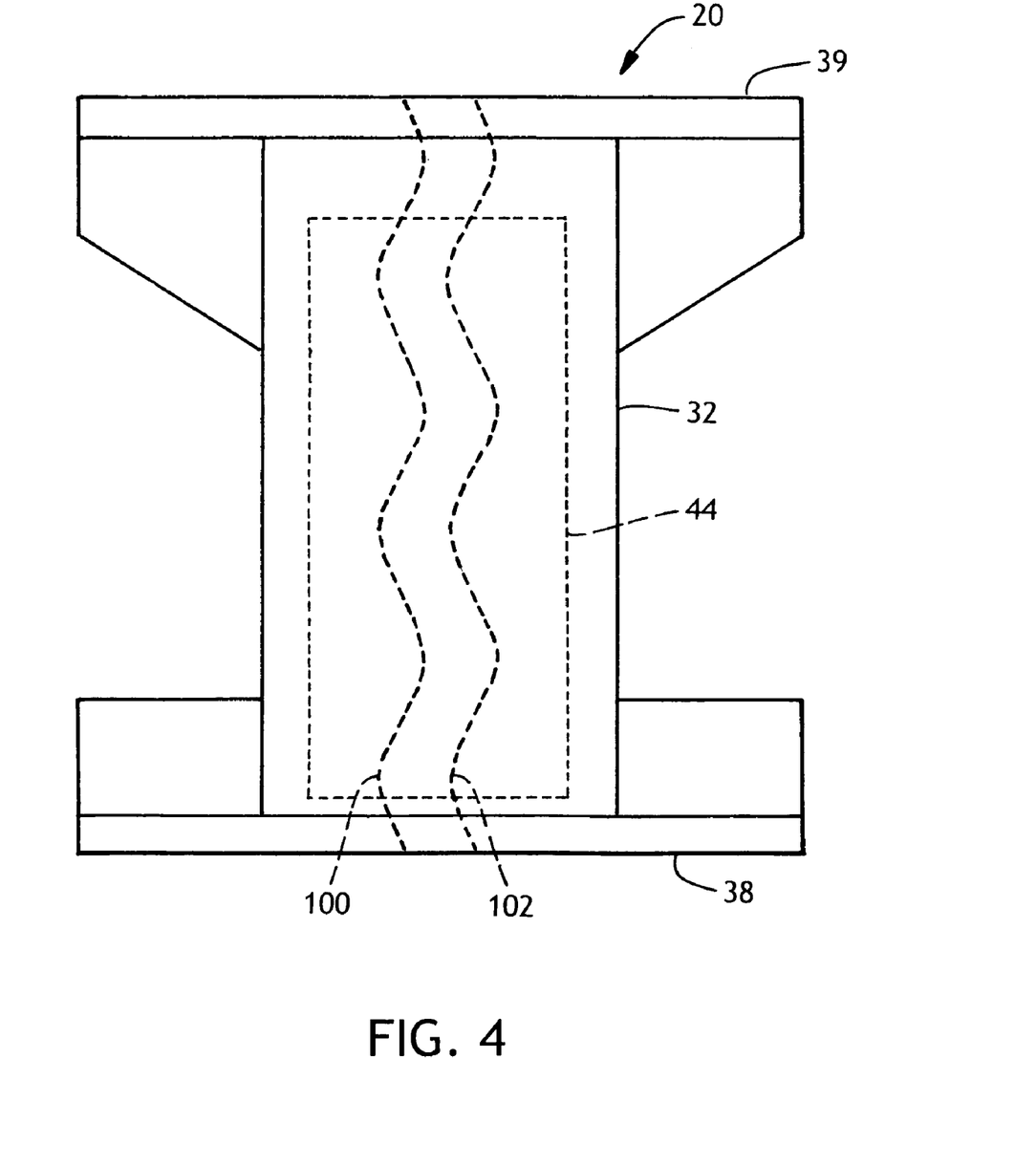
FIG. 4 is a schematic plan view of still another aspect of the absorbent article of FIG. 1.

The arrangement of the antenna 120 can also be varied to optimize the antenna's performance. The length of antenna 120 can be adjusted using process controls to tune or detune the antenna 120 to be a more effective transmitter. This tuning process can consider the output impedance of the transmitter circuitry. While this impedance is frequently 50 ohms, it may be that the antenna length is trimmed to achieve a match to another impedance, depending on the design of the transmitter. The antenna arrangement can include sinusoidal patterns (see FIG. 4) or straight runs. A sinusoidal or other non-linear pattern allows for a longer antenna 120 to be incorporated in a given space; this allows for a wider range of allowable antenna lengths and thus a wider range of tunable frequencies that can be used. This aspect is achieved in a insult-sensing absorbent article 20 by oscillating a conductive element 100 or 102 as it is incorporated into the insult-sensing absorbent article 20. This aspect is also achievable by printing the conductive element 100 or 102 in the insult-sensing absorbent article 20 using conductive inks. The antenna arrangement can be sine waves as shown in FIG. 4 or any other suitable shape including loops and other variations. In an alternative aspect for a folded dipole antenna 124, the distance between the antenna elements can be increased or decreased to tune the folded dipole antenna 124 for particular positions, products, or uses.

Selecting the appropriate placement of the antenna 120 within the insult-sensing absorbent article 20, also enhances signal efficiency and integrity. To avoid circumstances in which the antenna 120 is situated between two radio frequency-absorbing materials or is affected by near body transmission, the antenna 120 is preferably placed throughout and embedded in the insult-sensing absorbent article 20 to increase a signal's effective range and integrity. This embedding allows the antenna 120 to be linear (versus coiled), which is a more efficient design that requires less power to function reliably. In addition, this placement allows for a more compact design at lower cost. The antenna 120 is preferably placed in a spaced-apart arrangement from the body of the wearer to avoid signal interaction with the body. As with the case of antenna length, the output impedance of the transmitter may be adapted to account for such near-body antenna effects. Intimate contact with the body by the antenna 120 is generally to be avoided. Practically speaking, the natural bunching that occurs in the insult-sensing absorbent article 20 as it is worn affects adequate spacing.

Suitable materials for the antenna 120 include metals and other materials that provide sufficient impedance or efficient signal radiation. Such materials include metallized foils, wires, threads, conductive inks, and carbon fiber materials including conductive carbon fiber composites. Such materials are preferably of reasonable conductivity (i.e., low enough resistance per linear length to support these insult-sensing applications, such as, for example, 100 to 500 ohms or less per linear foot). Such materials allow for a proper medium for antenna electrical effectiveness and sufficient electron flow.

The signal from the antenna 120 can also be optimized by transmitting more than one signal, and by varying the temporal spacing between signals. For example, multiple, identical signals can be transmitted to increase the probability that at least one signal will be received. In another example, multiple signals can also be transmitted with increased temporal spacing to increase the probability that at least one signal will be received. In yet another example, a batch of multiple signals can be transmitted, followed by a temporal spacing, followed again by one or more additional signals. A combination of these examples or any other suitable signal pattern can also be used. Additional signal encoding and/or correlating may benefit signal integrity for near the body. Such signal patterns are especially important if the wearer is moving; movement by the wearer can affect the shape and shielding of the antenna, which could affect signal integrity. Varying the number and spacing of signal transmissions can accommodate antenna changes due to movement of the wearer.

For the aspects of the present disclosure in which a direct electrical/physical connection is made between the antenna 120 and the signaling device 110, such connection is preferably of low enough resistance so as not to significantly raise the total resistance of the load. Generally, this is accomplished because a connection that is stable enough to support accurate insult-sensing will also adequately support signaling for the antenna 120. The antenna 120 can be connected to the signaling device 110 electrically through the use of snaps, clips, or any other suitable electrical connection.

In other aspects of the present disclosure, a non-physical connection can be made between the antenna 120 and the signaling device 110. For example, the antenna 120 can be positioned in close proximity but not physically connected to a subsidiary antenna on the signaling device 110 and used as a means of reradiation of the signal. Reradiation is accomplished by the capacitive and inductive effects of the subsidiary antenna on the signaling device 110 coupling to the separate antenna 120 and thus reradiating the transmitted signal. This technique can approach the performance of the direct connection if the inductive and capacitive coupling is ideally tuned to the frequency of interest.

In another aspect of the present disclosure, the antenna 120 may be tuned while it is in close proximity to the body of a wearer to account for the body's effects on the signal. In addition, the body can be treated as a ground plane with the antenna 120 consequently tuned to the body. This approach can eliminate the parasitic capacitance effects of the body. Also, the body can be treated as a reradiating element as described above to benefit antenna performance. Each of these approaches can help to address the situation in which the body diminishes radio frequency transmission.

Tuning an antenna 120 such that its characteristics become close to ideal can help to minimize power consumption, maximize range, or both. The antennas 120 and approaches described herein can be used in any situation and in any form of personal care product that would require wireless monitoring including, for example, the wetness condition of a training pant, diaper, enuretic pant, feminine care product, or incontinence product; the health condition monitoring of the aforementioned; and the condition monitoring of a medical gown.

EXAMPLES

The effectiveness of these antenna technology approaches was tested with the following apparatus and conditions. Each of several training pants including an antenna 120 was placed on a mannequin filled with saline to simulate near body wireless transmission. The mannequin was then placed in 20 different positions. Received signal strength readings were taken at a distance of 33 feet with a handheld receiver connected to a spectrum analyzer. The handheld receiver was used to simulate near body receiving by a caregiver or a monitor.

Figure 5:
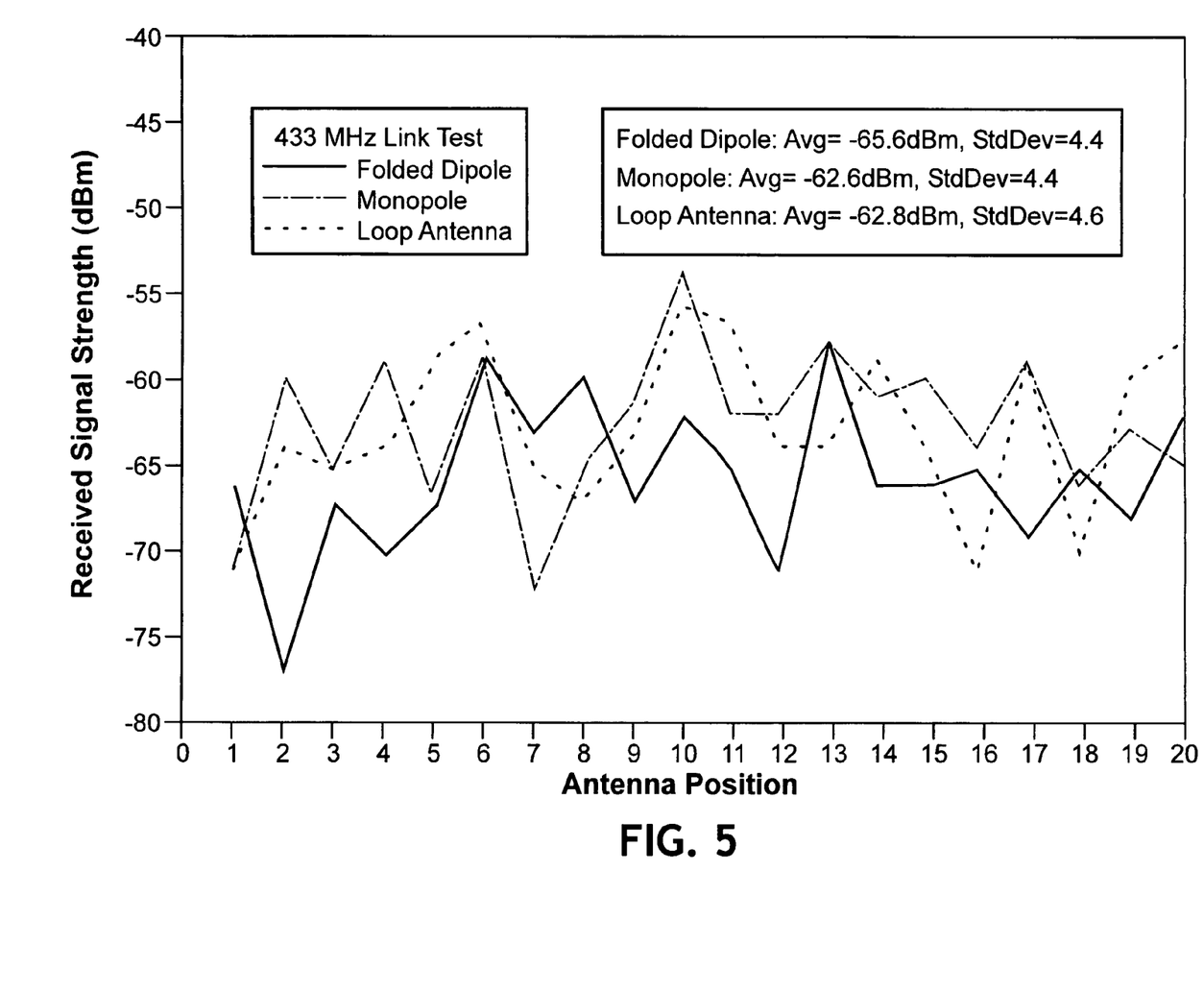
FIG. 5 represents the results of testing various aspects of the absorbent article of FIG. 1.

The results illustrated in FIG. 5 show the received signal strengths as a function of mannequin position of different antenna types in a training pant. These results were conducted with a carrier frequency of 433 MHz. The results show that each of the antenna designs radiates power effectively and similarly between each of the embodiments. Based on the link budget theorized for the transmitter and receiver, the path loss was within the link margin calculated; therefore, the transmitter, using these antenna designs, could effectively transmit over a longer range (e.g., 100 ft.). The statistics are posted in the legend of the graph and show that overall, each of the antennas 120 exhibits similar performance.

Figure 6:
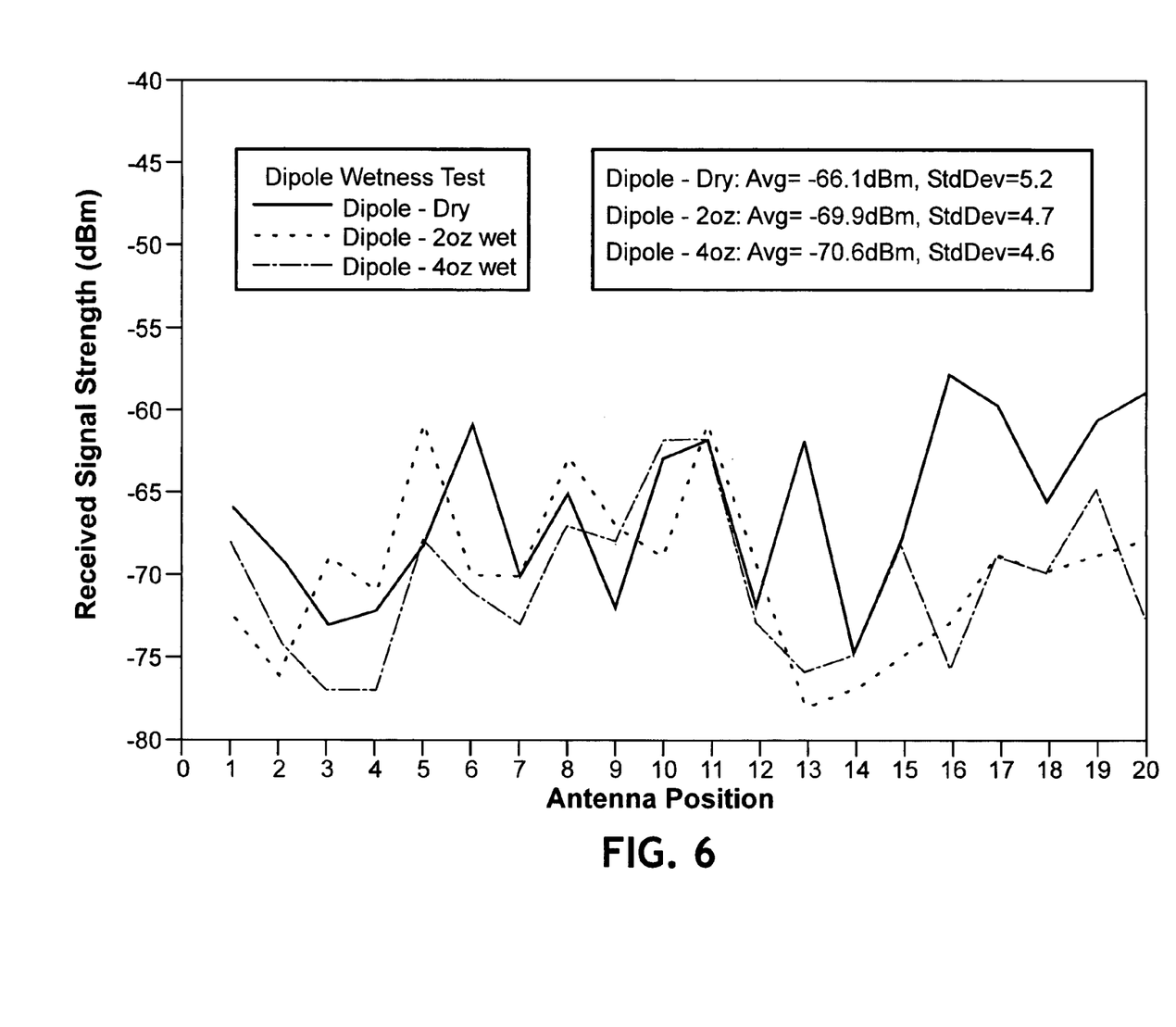
FIG. 6 represents the results of testing various other aspects of the absorbent article of FIG. 1.

Because the conductive elements within the training pant are in some examples the same as the conductors providing a wetness condition indication, the tests were repeated with the samples wetted to simulate an insulted pant. FIG. 6 illustrates the results of the wetted product test with the folded dipole design. The wet article antenna results are similar to those of the dry article showing only a little deviance in the average receiving signal strength but overall effective radiation under these conditions.

These and other modifications and variations to the present disclosure may be practiced by those of ordinary skill in the art, without departing from the spirit and scope of the present disclosure, which is more particularly set forth in the appended claims. In addition, it should be understood that aspects of the various aspects of the present disclosure may be interchanged either in whole or in part. Furthermore, those of ordinary skill in the art will appreciate that the foregoing description is by way of example only, and is not intended to limit the disclosure so further described in such appended claims.

What is claimed is:

1. A method for indicating an insult to an absorbent article to be worn by a wearer, the method comprising:
providing an absorbent article including an absorbent assembly disposed between an outercover and a bodyside liner, inner and outer surfaces, and an insult-sensing conductive element at least partially disposed between the outercover and the bodyside liner such that an insult must pass through the bodyside liner to contact the conductive element, wherein the conductive element is in fluid communication with the absorbent assembly;
providing a signaling device including
a transmitter configured to be removably attachable to the inner or outer surface of the absorbent article, the transmitter coupled to the insult-sensing conductive element and including a power source, wherein the conductive element is a transmitting antenna for the transmitter, and
a receiver separate from the absorbent article, the receiver configured to receive wirelessly a signal from the transmitting antenna, wherein the transmitter and receiver are separate and discrete units of the signaling device, the signaling device being configured to indicate the presence of a body fluid in the article, wherein the transmitter is adapted to transmit a signal via the transmitting antenna; and
maximizing the receivability of the signal by optimizing an aspect of the transmitter or the transmitting antenna, wherein optimizing includes tuning the transmitting antenna when the article is in close proximity to the wearer, and wherein the transmitter via the transmitting antenna transmits at a frequency between 1 GHz and 100 MHz.

2. The method of claim 1, wherein optimizing includes selecting an optimized frequency of the signal.

3. The method of claim 1, wherein the antenna has a length, wherein the signal has a wavelength, and wherein optimizing includes selecting an antenna length to correspond to the wavelength.

4. The method of claim 3, wherein the antenna length is one-quarter of the wavelength.

5. The method of claim 1, wherein the antenna is not in skin-contact with the wearer when the article is worn by the wearer.

6. The method of claim 1, wherein optimizing includes transmitting at least two signals for the same insult.

7. The method of claim 1, wherein optimizing includes transmitting a plurality of signals with a first pause between each signal, and transmitting an additional signal after a second pause, wherein the second pause is longer than each of the first pauses.

8. The method of claim 1, wherein the antenna is not in physical contact with the signaling device.

9. The method of claim 1, wherein the transmitting antenna includes a folded dipole antenna.

10. The method of claim 1, wherein the transmitting antenna includes a monopole antenna.

11. The method of claim 1, wherein the transmitting antenna includes a loop antenna.

12. A method for indicating an insult to an absorbent article to be worn by a wearer, the method comprising:
providing an absorbent article including an absorbent assembly disposed between an outercover and a bodyside liner, inner and outer surfaces, and an insult-sensing conductive element at least partially disposed between the outercover and the bodyside liner such that an insult must pass through the bodyside liner to contact the conductive element, wherein the conductive element is in fluid communication with the absorbent assembly;
providing a signaling device including
a transmitter configured to be removably attachable to the inner or outer surface of the absorbent article, the transmitter coupled to the insult-sensing conductive element and including a power source, wherein the conductive element is a transmitting antenna for the transmitter, and wherein the transmitting antenna is adapted to use the wearer as a ground plane, and
a receiver separate from the absorbent article, the receiver configured to receive wirelessly a signal from the transmitting antenna, wherein the transmitter and receiver are separate and discrete units of the signaling device, the signaling device being configured to indicate the presence of a body fluid in the article, wherein the transmitter is adapted to transmit a signal via the transmitting antenna; and
maximizing the receivability of the signal by optimizing an aspect of the transmitter or the transmitting antenna, wherein the transmitter via the transmitting antenna transmits at a frequency between 1 GHz and 100 MHz.

13. A method for indicating an insult to an absorbent article to be worn by a wearer, the method comprising:
providing an absorbent article including an absorbent assembly disposed between an outercover and a bodyside liner, inner and outer surfaces, and an insult-sensing conductive element at least partially disposed between the outercover and the bodyside liner such that an insult must pass through the bodyside liner to contact the conductive element, wherein the conductive element is in fluid communication with the absorbent assembly;
providing a signaling device including
a transmitter configured to be removably attachable to the inner or outer surface of the absorbent article, the transmitter coupled to the insult-sensing conductive element and including a power source, wherein the conductive element is a transmitting antenna for the transmitter and wherein the transmitting antenna is adapted to use the wearer as a reradiation element, and
a receiver separate from the absorbent article, the receiver configured to receive wirelessly a signal from the transmitting antenna, wherein the transmitter and receiver are separate and discrete units of the signaling device, the signaling device being configured to indicate the presence of a body fluid in the article, wherein the transmitter is adapted to transmit a signal via the transmitting antenna; and
maximizing the receivability of the signal by optimizing an aspect of the transmitter or the transmitting antenna, wherein the transmitter via the transmitting antenna transmits at a frequency between 1 GHz and 100 MHz.

* * * * *